(12) United States Patent
Stedele

(10) Patent No.: US 9,336,590 B2
(45) Date of Patent: May 10, 2016

(54) ADVANCED FIBER TRACKING AND MEDICAL NAVIGATION IN A BRAIN

(75) Inventor: Katrin Stedele, Munich (DE)

(73) Assignee: Brainlab AG, Feldkirchen (DE)

( * ) Notice: Subject to any disclaimer, the term of this patent is extended or adjusted under 35 U.S.C. 154(b) by 288 days.

(21) Appl. No.: 13/824,536

(22) PCT Filed: Sep. 28, 2010

(86) PCT No.: PCT/EP2010/064293
§ 371 (c)(1),
(2), (4) Date: Mar. 18, 2013

(87) PCT Pub. No.: WO2012/041364
PCT Pub. Date: Apr. 5, 2012

(65) Prior Publication Data
US 2013/0279772 A1   Oct. 24, 2013

(51) Int. Cl.
*G06K 9/00* (2006.01)
*G06T 7/00* (2006.01)
*A61B 19/00* (2006.01)

(52) U.S. Cl.
CPC .............. *G06T 7/0012* (2013.01); *A61B 19/50* (2013.01); *G06T 7/0081* (2013.01); *G06T 7/0089* (2013.01); *A61B 19/5244* (2013.01); *A61B 2019/505* (2013.01); *A61B 2019/5236* (2013.01); *A61B 2019/5289* (2013.01); *A61B 2019/566* (2013.01); *G06T 2207/10092* (2013.01); *G06T 2207/20128* (2013.01); *G06T 2207/20141* (2013.01); *G06T 2207/20156* (2013.01); *G06T 2207/30016* (2013.01)

(58) Field of Classification Search
None
See application file for complete search history.

(56) References Cited

U.S. PATENT DOCUMENTS

| | | | | |
|---|---|---|---|---|
| 4,051,845 A * | 10/1977 | Collins | ........................ | 128/855 |
| 4,276,697 A * | 7/1981 | Drake et al. | .................... | 33/644 |
| 6,249,595 B1 * | 6/2001 | Foxall | .............. | G01R 33/56554 |
| | | | | 382/128 |
| 6,526,415 B2 * | 2/2003 | Smith | ............... | G06F 17/30017 |
| 2007/0217664 A1 | 9/2007 | Flipo et al. | | |
| 2009/0005678 A1 | 1/2009 | Schmiedehausen et al. | | |
| 2009/0171184 A1 * | 7/2009 | Jenkins et al. | ................. | 600/411 |
| 2010/0079140 A1 * | 4/2010 | Holthuizen et al. | .......... | 324/307 |
| 2013/0279772 A1 * | 10/2013 | Stedele | .................. | A61B 19/50 |
| | | | | 382/128 |

OTHER PUBLICATIONS

International Search Report for International Application No. PCT/EP2010/064293 dated Sep. 28, 2010.
O'Donnell et al., "Automatic Tractography Segmentation Using a High-Dimensional White Matter Atlas", IEEE Transactions on Medical Imaging, vol. 26, No. 11, Nov. 2007, pp. 1562-1575.
Pham et al., "Current Methods in Medical Image Segmentation", Annual Review of Biomedical Engineering, vol. 2, Aug. 2000, pp. 315-337.
Damon et al., "Diffusion-Tensor MRI Based Skeletal Muscle Fiber Tracking", http://www.ncbi.nlm.nih.gov/pmc/articles/PMC4241547, Imaging Med., Nov. 2011, pp. 675-687.

(Continued)

*Primary Examiner* — Nancy Bitar
(74) *Attorney, Agent, or Firm* — Tucker Ellis LLP

(57) ABSTRACT

A method for finding fibers in image data of a brain, comprising the steps of: matching (S2) a functional atlas of the brain to an image data set which represents a medical image of the brain; performing functional atlas segmentation (S3) in order to segment the image data set into functional areas; using (S4, S8) the segmented image data set to determine at least one seed point for a fiber tracking algorithm; and - performing (S5) fiber tracking in order to find the fiber.

11 Claims, 3 Drawing Sheets

(56) References Cited

OTHER PUBLICATIONS

Figure 1:
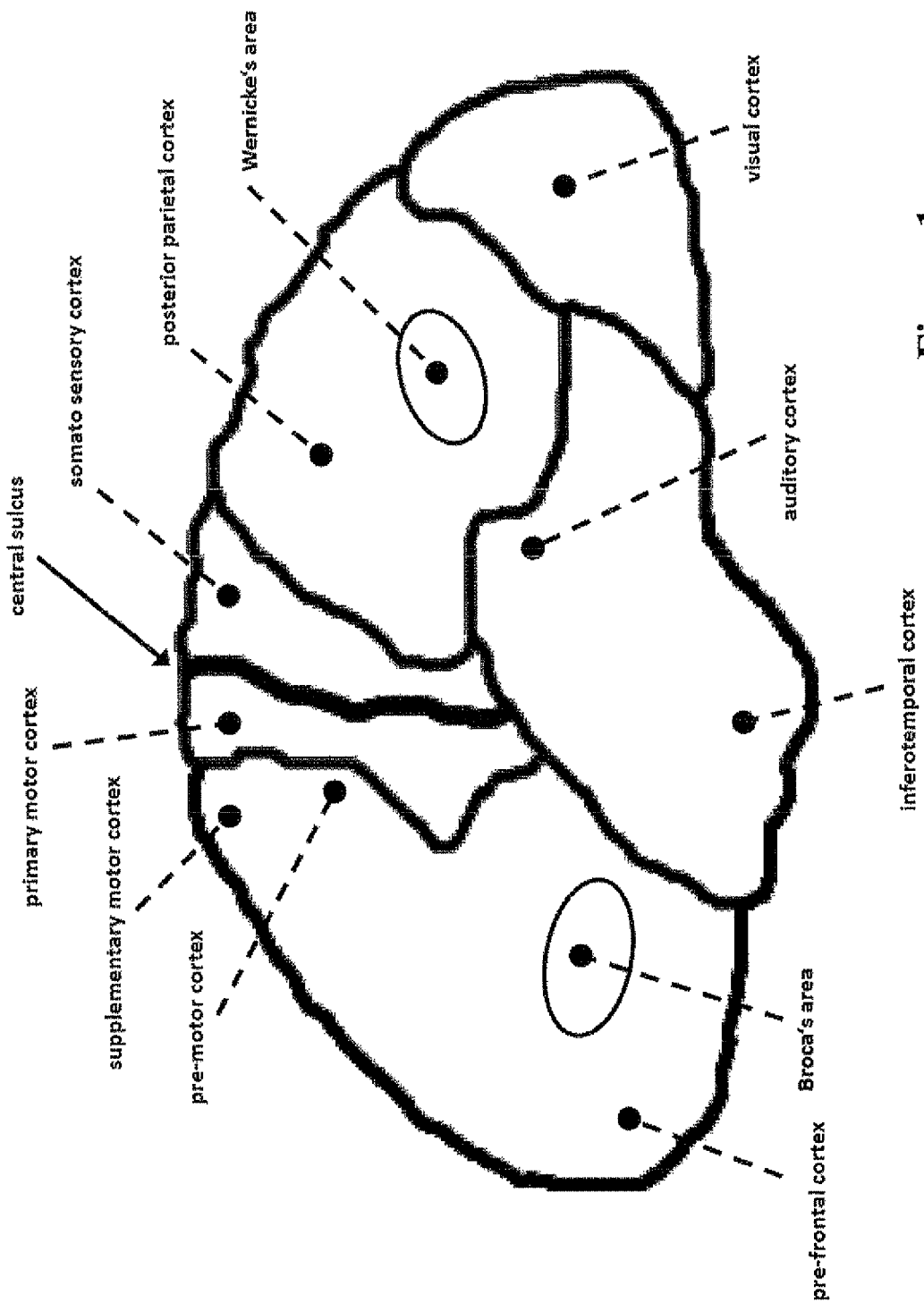

Mori et al., "Three-Dimensional Tracking of Axonal Projections in the Brain by Magnetic Resonance Imaging", The American Neurological Association, vol. 45, No. 2, Feb. 1999, pp. 265-269.

Mori et al., "Fiber tracking: principles and strategies—a technical review", NMR in Biomedicine, 2002, 15, pp. 468-480.

Diffusion Tensor Imaging (DTI)—Fiber Tracking—Imagilys, http://www.imagilys.com/diffusion-tensor-imaging-dti.

\* cited by examiner

ADVANCED FIBER TRACKING AND MEDICAL NAVIGATION IN A BRAIN

This application is a national phase of International Application No. PCT/EP2010/064293 filed Sep. 28, 2010 and published in the English language.

The present invention relates to a method for finding fibers in image data of a brain, a method for enabling the medical navigation of a brain, systems for performing these methods and a computer program for implementing the methods. Within the framework of the present invention, "finding" is in particular intended to also include the meanings of "locating" and "identifying". The term "fiber" can mean a single fiber or a bundle of fibers.

In recent years, brain surgery has become increasingly image-guided. In general, image-guided surgery allows a surgeon to track a medical instrument using images generated prior to or during an operation. Since the medical instrument can be navigated within the patient's body, this approach is also called surgical or medical navigation.

During navigation, critical structures have to be avoided. In the case of brain surgery, such structures include fibers such as the visual nerve, which is also called the optic nerve. It is therefore advantageous to find fibers in image data of a brain in order to be able to avoid these fibers during navigation.

The present invention relates to a method for enabling the medical navigation of a brain and finding fibers in image data of a brain. Methods, systems and computer programs according to the present invention are specified in the independent claims. Advantageous embodiments are described in the dependent claims. Common to all the independent claims is the utilisation of a functional atlas of the brain.

An atlas typically consists of a plurality of generic models of objects, wherein the generic models of the objects together form a complex structure. The atlas of a femur, for example, can comprise the head, the neck, the body, the greater trochanter, the lesser trochanter and the lower extremity as objects which make up the complete structure. The atlas of a brain, for example, can comprise the telencephalon, the cerebellum, the diencephalons, the pans, the mesencephalon and the medulla as the objects which make up the complex structure. One application of an atlas is in the segmentation of medical images, wherein the atlas is matched to medical image data and wherein by comparing the image data with the matched atlas, a point (a pixel or voxel) of the image data can be assigned to an object of the matched atlas, thereby segmenting the image data into objects.

In a functional atlas, the structure represented by the atlas is divided into functional areas rather than physical components. In a brain, for example, typical functional areas include the speech centre and the visual centre. However, a functional atlas can optionally also include anatomical landmarks. In a brain, for example, typical anatomical landmarks include gyri and sulci.

The present invention relates to a method for finding fibers in image data of a brain. The image data are available as an image data set which represents a medical image of the brain. The image data can for example be generated by x-ray, CT or MRI. The image data consist of points, i.e. pixels or voxels, in particular a two-dimensional or three-dimensional array of points.

In a first step, a functional atlas of the brain is matched to the image data set. This means that the geometry of the functional atlas is adapted such that the atlas matches the brain in the image data set. Matching is in particular performed using elastic or rigid image fusion.

In a following step, so-called functional atlas segmentation is performed in order to segment the image data set into functional areas. In this step, a function of the brain is assigned to each point (pixel or voxel) in the image data set of the brain.

In a following step, the segmented image data set is used to determine at least one seed point for the fiber tracking algorithm. Fiber tracking is then performed in order to find the fiber. The method optionally includes the additional step of providing the found fiber to a medical navigation process.

Fiber tracking can be used to find neural structures. Typically, the fiber tracking algorithm starts from a seed point in a region of interest (ROI) and follows the fiber step-by-step. If for example the visual nerve is to be found, the fiber tracking algorithm starts for example from a seed point in the visible part of the visual nerve, which can be identified using conventional atlas segmentation, and iteratively follows the visual nerve from point to point In a typical approach, diffusion tensor imaging (DTI) data is used in the fiber tracking algorithm, Diffusion Tensor imaging is based on the measurement of diffusion anisotropy in the brain using diffusion-weighted images which have been scanned in several directions. Such scans can be used to obtain information about the local diffusion of water molecules. Since water diffusion would be isotropic in uniform tissue, anisotropic regions reflect areas of different density, and in particular borders between areas of distinct density. Water molecules moving along neural pathways, i.e. fibers, can thus be tracked by following the major diffusion direction, as long as the fractional anisotropy value is over a certain threshold. The fiber is followed step-by-step by following the principal diffusion direction.

For the purpose of fiber tracking, in particular in order to find a bundle of fibers, a plurality of seed points are preferably determined. In particular, several seed points are located in the same functional area, i.e. the same region of interest. The seed points are preferably located in at least two distinct regions of interest, i.e. in particular, in distinct functional areas. This is particularly useful if the seed points mark distinct ends of the fiber or of a part of the fiber. The fiber or part of a fiber can then be tracked, starting from two opposite ends, wherein the paths which start from these ends approach each other or grow towards each other. Compared to using only one seed point, this reduces the probability of tracking the wrong fiber path instead of the correct one.

In one embodiment of the invention, determining a seed point involves using a point in an area of the segmented image data set as a seed point. This means that the seed point is located within the functional area. The seed point can be a start point, an end point or an intermediate point of the fiber which is to be found. This embodiment is thus one in which the segmented image data set is directly used.

In an alternative embodiment, determining a seed point involves using the segmented image data set to process a functional MRI data set and then using a point in a functional area of the processed functional MRI data set as the seed point. This is an indirect approach in which the segmented image data is used to process, in particular validate, another data set from which the seed point is then derived.

A functional magnetic resonance imaging (MRI) data set is an enhanced MRI data set which is obtained by selectively stimulating the brain, for example by issuing controlled sensory stimulations to the patient or by giving the patient a particular task to perform. An area of the brain showing increased activity during the stimulation is a functional area related to said stimulation. Activity is for example detected by correlating the measured MRI signal over a certain period of time with a reference signal. An area is considered stimulated if the correlation value is larger than a certain threshold.

Preferably, the functional MRI data set is generated by utilising the blood oxygen level dependent (BOLD) effect. The BOLD effect is caused by the patient performing different motoric or cognitive tasks in the MR scanner during a functional experiment, thus inducing activation which leads to complex local changes in relative blood oxygenation and changes in the local cerebral blood flow. Since the MR signal of blood varies slightly depending on the level of oxygenation, the BOLD effect can be visualised using appropriate MR scanning sequences.

The problem with BOLD MRI mapping is that the variation in the MR signal is rather small, which can lead to false positives, i.e. an erroneous detection of an area as belonging to a functional area, in particular due to a noisy signal. By processing the functional MRI data set using the segmented image data set, such false positives can be filtered out, i.e. the functional MRI data set can be validated. In particular, processing is based on generating the intersection of a functional area in the functional MRI data set and the corresponding functional area in the segmented image data set. Some or all areas, or parts of areas, in the MRI data set not belonging to the intersection are excised from the functional MRI data set. Additionally or alternatively, the threshold used for deciding whether an area is being stimulated or not is adapted by comparing the functional MRI data set with the segmented image data set.

The method optionally comprises the additional step of using the found fiber to adapt at least one of the functional atlas, the functional atlas segmentation process, an anatomical atlas or an anatomical atlas segmentation process. If the (functional or anatomical) atlas contains a template for the fiber, then this template can be adapted to the fiber as actually present in the brain and found in the corresponding image data set. In addition or as an alternative to modifying the atlas, the segmentation process based on the atlas can be adapted, for example by modifying the rules of the segmentation process. This additional step is a feedback step which helps to improve (functional) atlas segmentation for the next application of the method.

Fiber tracking is a preferred but not essential preparatory step for navigation. The present invention also relates to a method for enabling the medical navigation of a brain. This method comprises the steps of matching a functional atlas of the brain to an image data set which represents a medical image of the brain and performing functional atlas segmentation in order to segment the image data set into functional areas. These steps have already been explained above.

Instead of using the segmented image data set to determine seed points for fiber tracking, the method for enabling the medical navigation of a brain can also comprise the step of using the segmented image data for a medical navigation process. Omitting the fiber tracking step is particularly useful if navigation is to be performed in an area of the brain in which no important fibers are located or in which such fibers are already indicated in the functional atlas.

In one embodiment, using the segmented image data set involves providing the segmented image data set to the medical navigation process. Medical navigation is then based on the segmented image data.

In another embodiment, using the segmented image data set involves using the segmented image data set to process the functional MRI data set and providing the processed functional MRI data set to the medical navigation process. The functional MRI data set is preferably processed using the segmented image data as described above.

The method in accordance with the present invention is in particular a data processing method. The data processing method is preferably performed using technical means, in particular a computer. The computer in particular comprises a processor and a memory in order to process the data, in particular electronically. The method steps described are in particular performed by a computer. Determining or processing steps are in particular steps of determining data within the framework of the technical data processing method, in particular within the framework of a program. A computer is in particular any kind of data processing device. A computer can be a device which is generally thought of as such, for example desktop PCs or notebooks or netbooks, etc., but can also be any programmable apparatus, such as a mobile phone or an embedded processor. In particular, a computer can comprise a system (network) of "sub-computers", wherein each sub-computer represents a computer in its own right. A computer in particular comprises interfaces in order to receive data and/or to perform an analogue-to-digital conversion. The data are in particular data which represent physical properties and/or are generated from technical signals. The technical signals are in particular generated by means of technical detection devices and/or analytical devices.

The present invention also relates to a medical imaging system for finding fibers in image data of a brain, comprising a computer which is configured to perform the method for finding fibers in image data of a brain, as explained above. The invention also relates to a system for enabling the medical navigation of a brain, comprising a computer which is configured to perform the method for enabling the medical navigation of the brain, as explained above.

The present invention also relates to a program which, when running on a computer or when loaded onto a computer, causes the computer to perform one or more of the methods outlined above and/or to a program storage medium on which such a program is stored (in particular in a non-transitory form).

Within the framework of the invention, computer program elements can be embodied by hardware and/or software (this also includes firmware, resident software, micro-code, etc.). Within the framework of the invention, computer program elements can take the form of a computer program product which can be embodied by a computer-usable or computer-readable storage medium comprising computer-usable or computer-readable program instructions, "code" or a "computer program" embodied in said medium for use on or in connection with the instruction-executing system. Such a system can be a computer; a computer can be a data processing device comprising means for executing the computer program elements and/or the program in accordance with the invention. Within the framework of this invention, a computer-usable or computer-readable medium can be any medium which can include, store, communicate, propagate or transport the program for use on or in connection with the instruction-executing system, apparatus or device. The computer-usable or computer-readable medium can for example be, but is not limited to, an electronic, magnetic, optical, electromagnetic, infrared or semiconductor system, apparatus or device or a medium of propagation such as for example the Internet. The computer-usable or computer-readable medium could even for example be paper or another suitable medium onto which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

It is within the scope of the present invention to combine two or more embodiments described within this document to form another embodiment. Embodiments can be combined in their entirety or by selecting one or more features of an embodiment. Furthermore, features not essential to an embodiment can be omitted.

Figure 2:
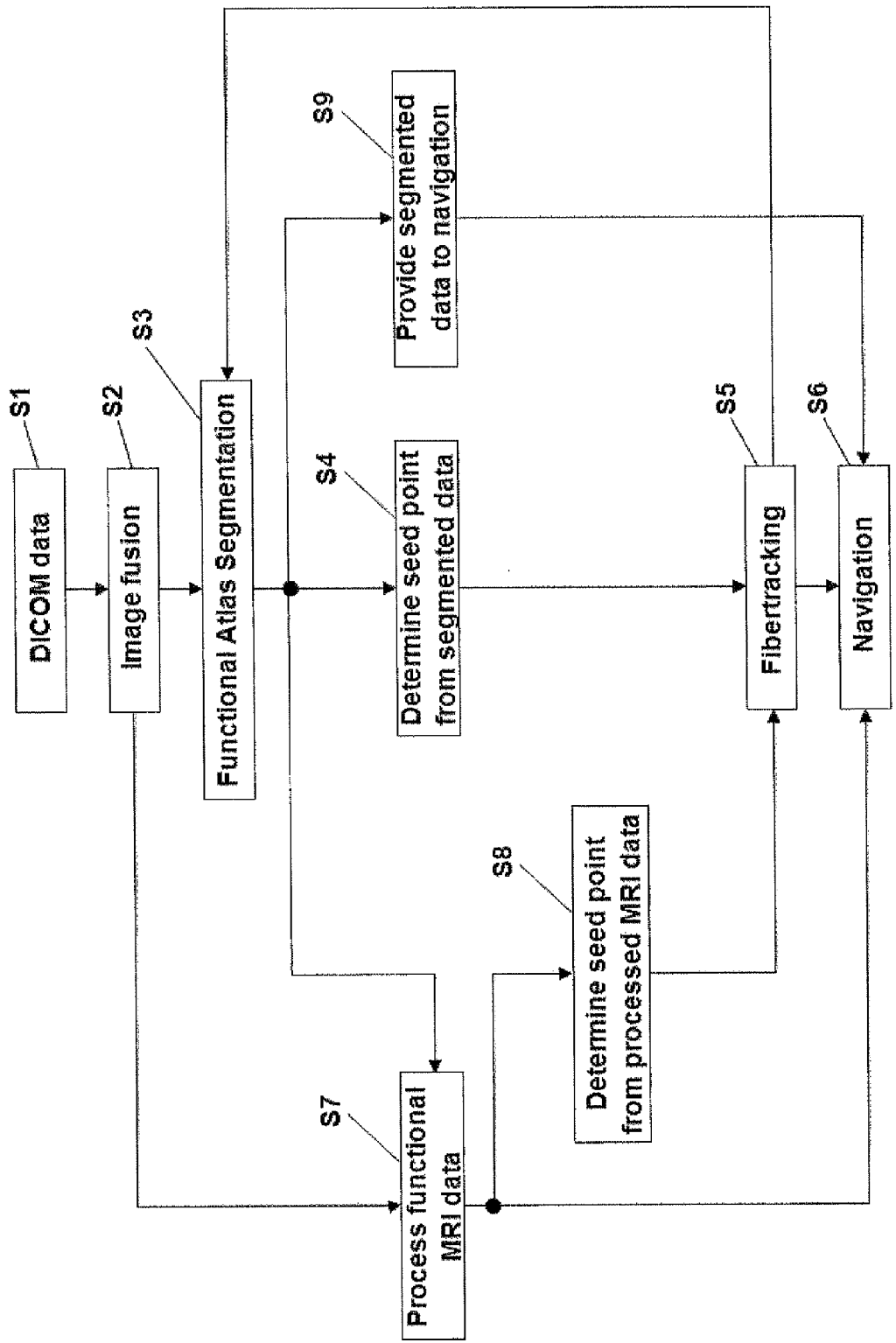

The present invention shall now be explained in more detail by referring to the appended figures, which show:

FIG. 1 a functional atlas of a brain;
FIG. 2 a workflow using a functional atlas for preparing surgery; and
FIG. 3 a computer for performing the invention.

FIG. 1 schematically shows a view of a functional atlas of a brain. The atlas is a 2D or preferably 3D model of the brain. The brain is divided into a plurality of functional areas. A functional area consists of a set of neurons which provide a specific function of the brain. In the example of FIG. 1, the atlas comprises the pre-motor cortex, the supplementary motor cortex, the primary motor cortex, the somatosensory cortex, the posterior parietal cortex, the visual cortex, Wernicke's area, the auditory cortex, the inferotemporal cortex, Broca's area and the pre-frontal cortex as functional areas. However, the atlas can also comprise more, fewer and/or other functional areas. In addition, the functional atlas can also contain anatomical structures or objects.

FIG. 2 shows an example of a workflow for preparing a surgical brain operation. In the present example, preparing involves producing data which can be provided to a navigation process. In particular, preparing means finding one or more fibers in an image data set which represents the brain. Common to all paths in the workflow is the utilisation of a functional atlas of the brain.

In a first step S1, existing data such as medical image data are received. The received data can comprise a plurality of different (image) data sets. In the present example, the digital imaging and communication in medicine (DICOM) standard is used for exchanging data. However, any other suitable interface can be used. The received data comprise at least the functional atlas and an image data set which represents a medical image of a brain, but can also comprise DTI data and/or functional MRI data and/or other suitable data.

In a following step S2, image fusion is performed. This step at least consists of matching the functional atlas to the image data set. In general, all the suitable data sets which are available are co-registered in this step to match the received data to the patient.

In the next step S3, functional atlas segmentation is performed in order to segment the image data set into functional areas. This is achieved by mapping the functional areas in the matched functional atlas to the image data set.

After step S3, the workflow splits into multiple—in the present example, three—paths. The path chosen depends on the data available and/or the desired result of the workflow. Each path can be considered separately.

The central path of the workflow shall be described first. After the functional atlas segmentation in step S3, at least one seed point is determined from the segmented image data in step 54. The seed point is placed in a functional area, or region of interest (ROI), which is known to comprise a start point, an end point or an intermediate point of the fiber which is to be found. Preferably, a plurality of seed points which in particular lie in at least two distinct functional areas are determined. The seed points are then provided to a step S5 in which fiber tracking is performed.

In step S5, the fiber is tracked step-by-step, starting from the seed point(s) provided. In the present example, fiber tracking is based on diffusion tensor imaging (DTI) which uses diffusion-weighted images in at least six diffusion directions. From the diffusion-weighted images, tensor values are calculated which provide information about the local diffusions in voxels or pixels of the image data set. Since fibers have a different density to the surrounding tissue, the local diffusion of water molecules at the border between a fiber and the surrounding tissue exhibits an anisotropy. From the direction of the anisotropy, which is represented by the diffusion tensors, the direction of a fiber at a certain pixel or voxel of the image data set can be determined.

Starting from a seed point, the direction of the fiber is determined from one or more diffusion tensors associated with the seed point. The neighbouring pixel or voxel in this direction is then regarded as belonging to the fiber and is used as a start point for a subsequent iteration step. From this starting point, the neighbouring pixel or voxel belonging to the fiber is determined on the basis of at least one diffusion tensor, the neighbouring pixel or voxel is then used as a start point in the next iteration step, and so on. Preferably, at least two seed points in at least two different regions of interest on opposite ends of the fiber or part of a fiber are used. The fiber or part of a fiber is then tracked, starting from these seed points, until a meeting point is found.

Once the fiber has been found, the task of the method according to the present invention is fulfilled. However, the found fiber can also then be provided to a medical navigation process which is performed in step S6, for example in order to avoid the fiber when navigating a medical instrument in the brain.

After the functional atlas segmentation in step S3, the workflow can branch onto the left-hand path if functional MRI data are available. In step S7, the functional MRI data are processed using the segmented image data set.

In general, the functional MRI data are generated by performing MRI on a patient while the patient performs different motoric or cognitive tasks. Neurons or areas of the brain which are stimulated while the task is performed are then assigned to a specific function. Preferably, a functional MRI data set is generated by using the blood oxygen level dependent (BOLD) effect.

Due to the small signal changes between an area being stimulated or not, it is necessary to repeat the measurement a number of times and/or to perform the measurement over a longer period of time. A decision as to whether an area is being activated by stimulation or not is based on a threshold value for a correlation value, this correlation value representing the correlation of the measured MRI data and reference data. However, an incorrect threshold could lead to suboptimal detection, and in particular false positives, due to noise in the MRI signal In accordance with the left-hand path of the workflow, the functional MRI data are processed in step S7. One way of processing the data is to adapt the threshold used for interpretation of the functional MRI data on the basis of a comparison of the functional MRI data and the segmented image data set. Another way is to excise false positives from the functional MRI data by calculating the intersection of corresponding functional areas in the functional MRI data and the segmented image data set. The intersection can be performed for one area, multiple areas, all areas or parts of these areas.

The processed functional MRI data can then be directly provided to the medical navigation process in step S6. Another option is to determine at least one seed point from the processed functional MRI data in step S8. This determination is analogous to step S4, but uses the validated functional MRI data instead of the segmented image data set. The seed points determined in step S8 are then provided to the fiber tracking process in step S5.

A feedback link from the fiber tracking step S5 to the functional atlas segmentation step S3 is optionally provided. Using the fiber tracking results, the functional atlas can be adapted. Additionally or alternatively, the processing rules for functional atlas segmentation can be adapted on the basis of the results of the fiber tracking step S5.

After the functional atlas segmentation step S3, the workflow can branch onto the right-hand path of the workflow. In step S9 of this third path, the segmented image data set is provided to the navigation process of step S6. This means that the segmented image data set can be used for navigation without finding a fiber in the image data set beforehand. This is particularly useful if the functional atlas comprises fibers which do not necessarily have to be validated by fiber tracking.

Figure 3:
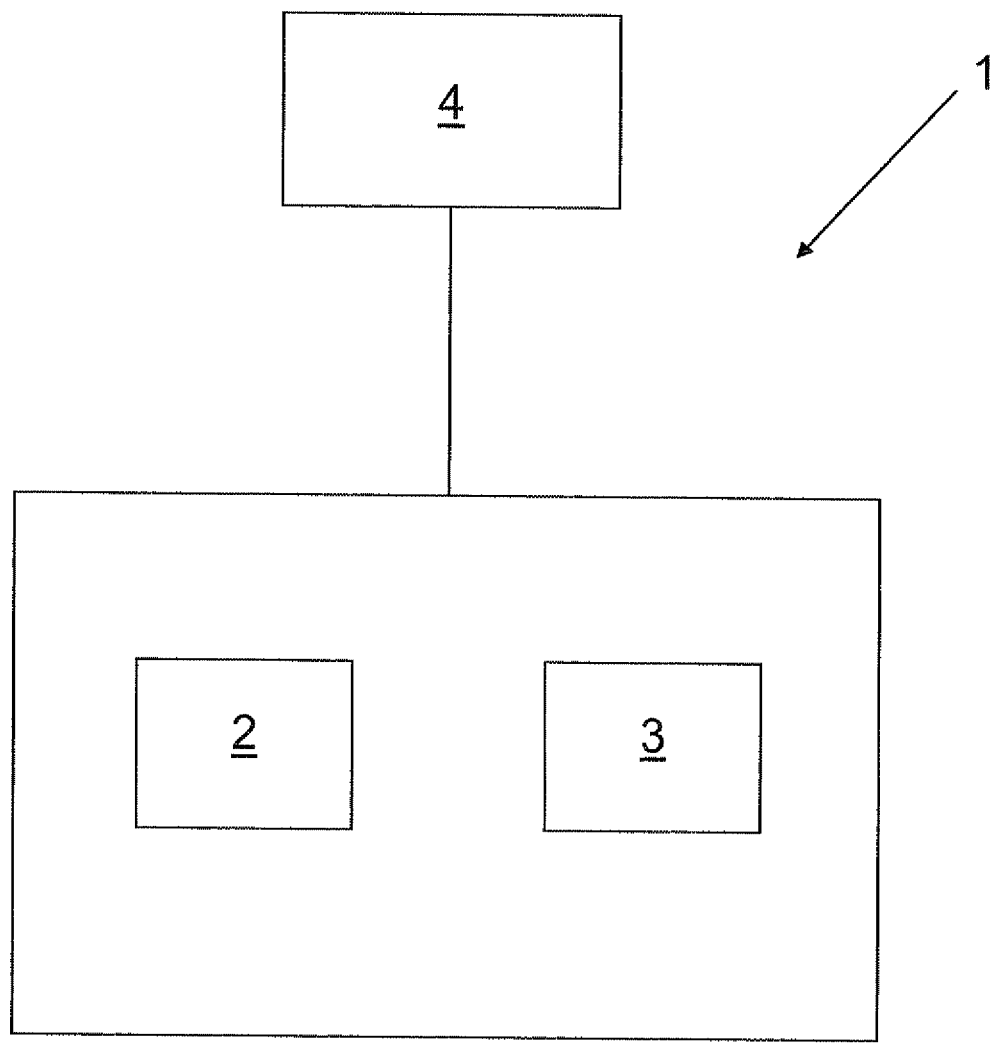

FIG. 3 shows a schematic representation of a computer 1 for implementing the present invention. The computer 1 comprises a central processing unit 2 for performing the method steps according to the present invention. An interface 3 is provided for receiving data, and a display device 4 is provided for displaying images.

The interface 3 can be used to receive the functional atlas and/or the image data set which represents the brain. The interface 3 can for example be used to connect the computer 1 to a medical imaging system such as an x-ray, CT or MRT apparatus. The interface 3 can also serve as an interface for an internal or external storage medium which stores the functional atlas and/or the image data set. The display device 4 can be used to display the image data set, preferably with a fiber highlighted as applicable. A surgeon or other suitable participant can then judge whether or not the fiber tracking result is plausible or whether fiber tracking is to be performed again, for example on the basis of modified seed points. The display device 4 can also be used by the navigation process to show the position of a medical instrument within the brain. Using an input device (not shown) of the computer 1, the surgeon can input data into the computer 1, such as for example a new threshold for the functional MRI procedure and/or modifications to the seed points used for fiber tracking.

An adaptor can be used to assemble multiple parts of the system or to attach the system to another device. Such an adaptor is also part of this invention. An adaptor for fixing a (medical) apparatus to one or two support structures is characterised in that the adaptor is constructed in three parts from a bearing part and two support parts, wherein the bearing part can be connected to the medical apparatus, the first support part can be connected to a first support structure and the second support part can be connected to a second support structure, and wherein the adaptor can assume at least three states, wherein: in the first state, the bearing part is connected, free of clearance, to the first support part only; in the second state, the bearing part is connected, free of clearance, to the second support part only; and in the third state, the bearing part is connected, free of clearance, to the first support part and the second support part.

The invention claimed is:

1. A method for finding a fiber in image data of an associated physical brain, the method comprising:
    storing in a non-transient memory storage medium a functional atlas of a generic brain, wherein an atlas structure represented by the functional atlas comprises the generic brain divided into one or more functional areas rather than into physical components or areas, each of the one or more functional areas being representative of a set of neurons which provide a specific function of the generic brain:
    matching the functional atlas of the generic brain to an image data set which represents a medical image of the associated physical brain, the matching comprising adapting a geometry of the functional atlas of the generic brain such that the functional atlas as an adapted functional atlas matches the physical brain in the image data set;
    performing functional atlas segmentation in accordance with the adapting of the functional atlas to the adapted functional atlas to segment the image data set into the one or more functional areas of the associated physical brain resulting in a segmented image data set;
    determining at least one seed point in the segmented image data set for use by a fiber tracking algorithm; and
    performing fiber tracking in the image data, using the fiber tracking algorithm and the at least one seed point, to find the fiber by tracking the fiber step-by-step starting from the seed point.

2. The method of claim 1, wherein the determining the seed point comprises using a point in an area of the segmented image data set as the seed point, said area comprising a start point, an end point or an intermediate point of the fiber which is to be found.

3. The method of claim 1, wherein the determining the seed point comprises using the segmented image data set to process a functional magnetic resonance imaging (MRI) data set and then using a point in a functional area of the processed functional MRI data set as the seed point.

4. The method of claim 3, further comprising generating the functional MRI data set by utilizing a blood oxygen level dependent (BOLD) effect.

5. The method of claim 1, further comprising:
    using the found fiber to adapt at least one of the functional atlas, the functional atlas segmentation process, an anatomical atlas or an anatomical atlas segmentation process.

6. The method of claim 1, further comprising performing the fiber tracking based on diffusion tensor imaging.

7. The method of claim 1, further comprising:
    providing the found fiber to a medical navigation process.

8. The method of claim 1, wherein the determining the at least one seed point comprises determining a plurality of seed points.

9. The method of claim 8, wherein the determining the plurality of seed points comprises determining at least two seed points located in at least two distinct functional areas.

10. A medical imaging system for finding a fiber in image data of an associated physical brain, comprising a computer which is configured to perform the method of claim 1.

11. A non-transitory computer-readable program storage medium storing a computer program which, when running on a computer or when loaded onto a computer, causes the computer to perform a method for finding a fiber in image data of a physical brain, comprising:
    storing in a non-transient memory storage medium a functional atlas of a generic brain, wherein an atlas structure represented by the functional atlas comprises the generic brain divided into one or more functional areas rather than into physical components or areas, each of the one or more functional areas being representative of a set of neurons which provide a specific function of the generic brain:

matching the functional atlas of the generic brain to an image data set which represents a medical image of the associated physical brain, the matching comprising adapting a geometry of the functional atlas of the generic brain such that the functional atlas as an adapted functional atlas matches the physical brain in the image data set;

performing functional atlas segmentation in accordance with the adapting of the functional atlas to the adapted functional atlas to segment the image data set into the one or more functional areas of the associated physical brain resulting in a segmented image data set;

determining at least one seed point in the segmented image data set for use by a fiber tracking algorithm; and performing fiber tracking in the image data, using the fiber tracking algorithm and the at least one seed point, to find the fiber by tracking the fiber step-by-step starting from the seed point.

* * * * *